US008408461B2

(12) United States Patent
Modavis et al.

(10) Patent No.: US 8,408,461 B2
(45) Date of Patent: Apr. 2, 2013

(54) SYSTEM AND METHOD FOR IMAGE ANALYSIS POINTING-ERROR CORRECTION

(75) Inventors: Robert A. Modavis, Painted Post, NY (US); Garrett A. Piech, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 128 days.

(21) Appl. No.: 12/887,048

(22) Filed: Sep. 21, 2010

(65) Prior Publication Data

US 2011/0006116 A1  Jan. 13, 2011

Related U.S. Application Data

(62) Division of application No. 11/974,231, filed on Oct. 12, 2007, now Pat. No. 7,819,320.

(51) Int. Cl.
*G06K 5/00* (2006.01)
(52) U.S. Cl. ........ 235/435; 235/437; 235/438; 235/454; 356/400; 356/614; 356/615

(58) Field of Classification Search .................. 235/435, 235/437, 438, 454; 356/400, 614, 615
See application file for complete search history.

(56) References Cited

U.S. PATENT DOCUMENTS

| | | | |
|---|---|---|---|
| 5,581,638 A * | 12/1996 | Givens et al. ............... 382/294 |
| 5,628,320 A | 5/1997 | Teo ............................ 600/443 |
| 5,815,337 A | 9/1998 | Milo ............................ 360/75 |
| 6,512,868 B1 | 1/2003 | Foster et al. .................... 385/33 |
| 7,202,076 B2 | 4/2007 | Cunningham et al. ..... 435/287.2 |
| 7,217,574 B2 | 5/2007 | Pien et al. .................... 436/164 |
| 2001/0001580 A1 | 5/2001 | Rowe ........................... 359/204 |
| 2003/0175987 A1* | 9/2003 | Verdonk et al. .............. 436/172 |
| 2006/0001878 A1* | 1/2006 | Das et al. ...................... 356/400 |
| 2006/0013453 A1 | 1/2006 | Schneider et al. ............. 382/124 |
| 2006/0141611 A1* | 6/2006 | Frutos et al. ............... 435/287.2 |
| 2009/0027693 A1 | 1/2009 | Dailey et al. .................. 356/620 |
| 2010/0188723 A1* | 7/2010 | Cobb et al. .................. 359/226.2 |

* cited by examiner

*Primary Examiner* — Allyson Trail
(74) *Attorney, Agent, or Firm* — John L. Haack

(57) ABSTRACT

The disclosure relates to a system and a method for light beam interrogation of an optical biosensor and for monitoring a biological event on the biosensor for use, for example, in microplate image analysis. The system and method correct pointing-errors that can be encountered, for example, in scanning label-independent-detection biosensor applications.

2 Claims, 9 Drawing Sheets

SYSTEM AND METHOD FOR IMAGE ANALYSIS POINTING-ERROR CORRECTION

CROSS-REFERENCE TO RELATED APPLICATIONS

This application is a divisional of and claims the benefit of priority to U.S. patent application Ser. No. 11/974,231, filed on Oct. 12,2007, now U.S. Pat. No. 7,819,320 the content of which is relied upon and incorporated herein by reference in its entirety.

The entire disclosure of any publications, patents, and patent documents mentioned herein are incorporated by reference.

BACKGROUND

The disclosure relates to the field of biosensors for label independent detection (LID). More particularly the disclosure relates to optically scanned label independent detection biosensors and to a system and method for microplate image analysis.

SUMMARY

The disclosure provides a system and method for microplate image analysis pointing-error correction for use, for example, in an optically scanned label independent detection system.

DETAILED DESCRIPTION

Figure 1:
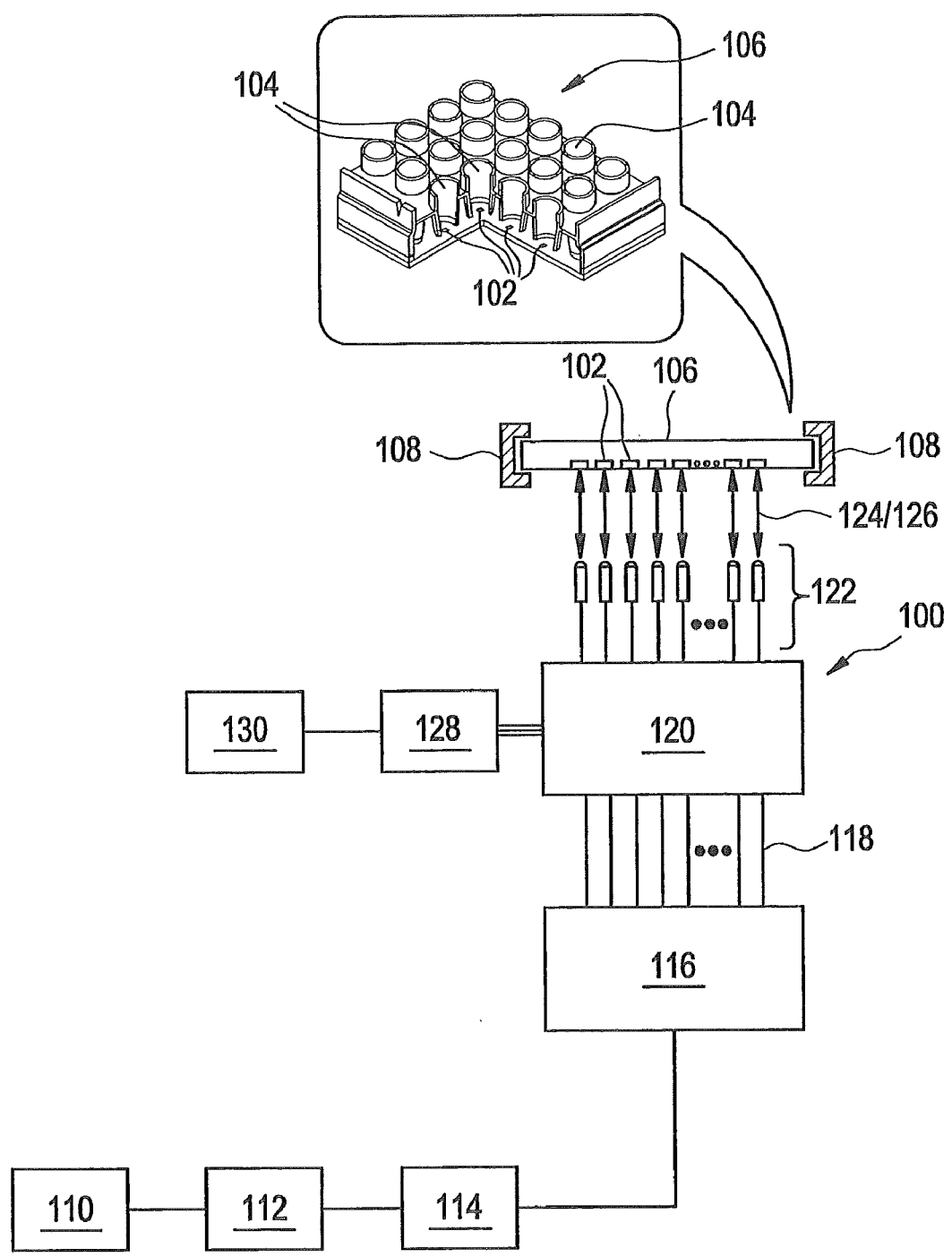
FIG. 1 shows exemplary optical reader system component, in embodiments of the disclosure.

Various embodiments of the disclosure will be described in detail with reference to drawings, if any. Reference to various embodiments does not limit the scope of the invention, which is limited only by the scope of the claims attached hereto. Additionally, any examples set forth in this specification are not limiting and merely set forth some of the many possible embodiments for the claimed invention.

Definitions

"Pointing-error" or like terms refer, for example, to variation in a scanner average beam spot location or position from an ideal or expected location on a biosensor grating as a result of variation in optical, mechanical, or both component properties as found, for example, in the optical imaging system of a microplate scanner. By processing the scanned image data the pointing-error (PE) for a region comprised of N scan lines can be reduced, or corrected, to a level given by:

$$PE_{corrected} = \pm(\Delta s/4)$$

where $PE_{corrected}$ is the corrected pointing-error and $\Delta s$ is the spacing (in y) between the adjacent scan lines. By eliminating scan lines from the analysis, the pointing-error, or average y-location, of an analysis region may be reduced. The pointing error may be reduced to this level provided that the actual pointing-error, $PE_{actual}$, obeys the relation:

$$|PE_{actual}| \leq (2N-1)\Delta s/4$$

where N is the number of equally spaced adjacent scan lines. If the scan lines are not equally spaced, y-pointing-error correction can still be accomplished but the above relations would need to be modified accordingly. If, for example, $\Delta s$ is 100 microns and N is 7, then an actual y-pointing-error of ±325 microns could be corrected to ±25 microns. However, the larger the y-pointing-error that needs to be corrected the fewer the number of scan lines that can be used for subsequent analysis. Therefore, it is advantageous to minimize the actual y-pointing-error to maximize the amount of data available for subsequent analysis.

"Micro-lense," "collimator-microlense," "beam collimator" or like terms refer, for example, to an optical system element which redirects rays of light from a light source, which rays or beams are used to interrogate a microplate.

"Scan," "scanning," "scanned," or like terms refer, for example, to a raster image data sample or sampling procedure.

"Develop," "developed," or like terms refer, for example, to a previously unused microplate or like substrate that is or has been contacted with a substance to create or test for an interaction between the microplate surface and the substance.

"Contact" or "contacting" or like terms refer to, for example, an instance of exposure by close physical contact of at least one substance to another substance, such as between a substrate such as the chemically or biologically modified surface of a microplate and a second substance such as an analyte or a ligand.

"Attach," "attachment," "adhere," "adhered," "immobilized," or like terms generally refer to immobilizing or fixing for example, by any physical-chemical interaction between two or more components or compounds, for example, a protein or like synthetic or natural biological, a surface modifier substance, a compatibilizer, a cell, a ligand candidate compound, and like entities within the scope of the disclosure, such as to a surface, such as by physical absorption, chemical bonding, and like attachment interactions, or combinations thereof. Examples of attachment interactions can include, for example, covalent, electrostatic, ionic, hydrogen, hydrophobic bonding, and like interactions, or combinations thereof. The type and extent of physical-chemical interaction that can be formed will vary depending upon the nature and disposition of the surface of biosurface and the particular chemicals or biologicals that contact the biosurface.

The indefinite article "a" or "an" and its corresponding definite article "the" as used herein means at least one, or one or more, unless specified otherwise.

"Include," "includes," or like terms mean including but not limited to.

"About" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and computational procedures used for scanning; through inadvertent error in these procedures; through differences in the manufacture, source, or purity of starting materials or ingredients used to carry out the methods; and like considerations. The term "about" also encompasses amounts that differ due to, for example, aging of a microplate formulation having a particular initial concentration, mixture, or surface topography, and amounts that differ due to processing a formulation with a particular initial concentration, mixture, or surface topography. Whether modified by the term "about" the claims appended hereto include equivalents to these quantities.

"Optional" or "optionally" or like terms generally refer to, for example, that the subsequently described event or circumstance can or cannot occur, and that the description includes instances where the event or circumstance occurs and instances where it does not.

"Consisting essentially of" in embodiments refers, for example, to a microplate surface composition or disposition, a system and method for measuring microplate surface composition or disposition, a system and method for measuring differences in microplate surface composition or disposition, a system and method for microplate image analysis, such as a biosensor in a microplate, and articles, devices, or apparatus of the disclosure, and can include the components or steps listed in the claim, plus other components or steps that do not materially affect the basic and novel properties of the composition, article, apparatus, system, and method of making and use of the disclosure, such as a particular reactant, a particular additive or ingredient, a particular agent, a particular surface modifier or condition, a particular ligand candidate, a particular equation or mathematical expression, or like structure, material, process, or computational variable selected. Items that may materially affect the basic properties of the components or steps of the disclosure, or that may impart undesirable characteristics to aspects of the present disclosure include, for example, increased false negatives;
increased false positives;
reduced yields in surface modification steps during the manufacture of microplates;
reduced assay measurement accuracy; or
heightened restrictions or narrower tolerance specifications for the placement of optional reference regions on the sensor surface.

Thus, the claimed invention may suitably comprise, consist of, or consist essentially of: a method for microplate image analysis including determining and correcting beam pointing-error; and a system for scanned label independent detection including an optical biosensor having a microplate, associated biosensor scan optics, and an image processor for determining and correcting beam pointing-error.

This application is related to the following commonly owned and assigned patent application documents:

U.S. patent application Ser. No. 11/027,547 filed Dec. 29, 2004, entitled "Spatially Scanned Optical Reader System and Method for Using Same," Publication No. US 20060141611 A1, published Jun. 29, 2006.

U.S. patent application Ser. No. 11/027,509, filed Dec. 29, 2004, entitled "Method for Creating a Reference Region and a Sample Region on a Biosensor and the Resulting Biosensor," Publication No. US 20040141527 A1, published Jun. 29, 2006, see for example FIG. 1 which illustrates three different methods for creating a reference region and a sample region on a single biosensor.

U.S. patent application Ser. No. 11/210,920, filed Aug. 23, 2005, entitled "Optical Reader System and Method for Monitoring and Correcting Lateral and Angular Misalignments of Label Independent Biosensors," Publication No. U.S. Pat. No. 20060139641 A1, published Jun. 29, 2006, mentions an optical reader system that uses a scanned optical beam to interrogate a biosensor to determine if a biomolecular binding event occurred on a surface of the biosensor. In embodiments, the optical reader system includes a light source, a detector and a processor (e.g., a computer, DSP, or like devices). The light source outputs an optical beam which is scanned across a moving biosensor and while this is happening the detector collects the optical beam which is reflected from the biosensor. The processor or computer processes the collected optical beam and records the resulting raw spectral or angle data which is a function of a position (and possibly time) on the biosensor. The processor can then analyze the raw data to create a spatial map of resonant wavelength (peak position) or resonant angle which indicates whether or not a biomolecular binding event occurred on the biosensor. Several other uses of the raw data are also described.

U.S. Patent Application Ser. No. 60/781,397, filed Mar. 10, 2006, entitled "Optimized Method for LID Biosensor Resonance Detection." now U.S. patent application Ser. No. 11/716,425, filed Mar. 9, 2007.

U.S. Patent Application Ser. No. 60/844,736, filed Sep. 9, 2006, entitled "Active Microplate Position Correction for Biosensors."

U.S. patent application Ser. No. 11/711,207, filed Feb. 27, 2007, entitled "Swept Wavelength Imaging Optical Interrogation System and Method for Using Same."

U.S. patent application Ser. No. 11/974,406, filed Oct. 12,2007 (concurrently herewith), entitled "SYSTEM AND METHOD FOR MICROPLATE IMAGE ANALYSIS."

In embodiments, the disclosure provides a method to correct microlense or "collimator-like" pointing-error, for example, in the y-axis, in the perpendicular x-axis, or both, in an optical reader, such as used in the Corning Epic® scanning label independent detection instrument. In embodiments, the "scan-axis" is typically along the x-axis and the y-axis is perpendicular to the scan-axis.

A factor that limits the size and location of where a reference pad or reference region of a sensor in a microplate can be placed is the axial pointing-error of the collimators (e.g., 16) that are used to interrogate a microplate. The collimators are aligned so that, for example, their y-axis component of pointing-error is typically within ±100 microns. When a 2D scan method of the disclosure is used to interrogate the sensor, it is possible to substantially reduce this y-pointing-error and to relax the specification tolerance on the y-direction location placement for the reference pad, or upon the placement of the grating sensor. These improvements enable in microplates to be produced more easily and at less cost.

In embodiments, the disclosure provides a method for correcting y-axis pointing-error when interrogating a microplate, such as with a two-dimensional algorithm. The pointing-error correction accomplished by the disclosed method provides several significant improvements including, for example, reduced false negatives;
reduced false positives;
improved yields in the manufacture of microplates;
improved yields in microplate surface modification;
improved assay measurement accuracy;
relaxed tolerances or reduced tolerances for the placement of the chemically altered reference region, such as in the y-direction, which enables easier and less costly manufacture of microplates, such as those used in the commercially available Corning Epic® instrument; and
increased maximum allowable pointing-error of a collimator, for example, with a scan spacing in the y-axis of about 100 microns the pointing-error can be increased from ±100 microns to ±125 microns without any impact on the microplate sensor y-direction placement tolerance.

Thus, the method and system of the disclosure enable a relaxed manufacturing specification for microplate criteria since exact placement of reference regions in a microwell is relaxed or less critical. Accordingly, more microplates can be manufactured using the disclosed pointing-error correction method that can pass the specification tolerance and are acceptable for use in biosensor assays.

In embodiments, the disclosure provides a method and system for microplate image analysis including determining and correcting beam collimator pointing-error; and a scanned label-independent apparatus that includes an optical biosensor having a microplate, associated biosensor scan optics, and an image processor for detecting and correcting beam pointing-error.

In embodiments the method and system improve the performance of, for example, the Corning® Epic® analyzer, an automated biosensor system platform, using a superior microplate scan and data analysis method that can detect and correct beam pointing error. The method and system of the present disclosure, while having been demonstrated as being particularly useful, for example, in the Corning® Epic® analyzer, the method and system can be useful, for example, in any apparatus or method that involves beam pointing and concomitant pointing-errors, such as in image processing, and like applications.

In general, the pointing error of an imaging reader system can be corrected by first acquiring an image which is larger than the region which is to be integrated. Such an image is comprised of sampled data, or pixels, either along just a single (x-) axis in the case of a 1D scan, or two axes (x- and y-), in the case of a 2D scan. Before integrating the signal within a particular region of pixels, the data in the image is shifted to account for the pointing error. For example, if the pointing error is eight pixels in the horizontal axis and two pixels in the vertical axis, the data set would be shifted by eight pixels horizontally and two pixels vertically before integration. By correcting the data for beam pointing-error, precise spatial regions within the sensor may be measured, allowing more accurate biochemical measurements.

The pointing-error, or amount of shift to be applied to the data before processing, can be measured by using either a CCD detector, see for example Example 1, or a reference microplate, see for example Example 2. Similar to Example 2, any set of fiducial elements on the microplate may be used to measure the pointing-error of each beam. Such a measurement may even be made as part of the scan in which the wavelength or biochemical measurements are made.

In embodiments, the disclosure provides a method for y-axis beam pointing-error correction in an optical reader-scanner having pointing-error, the method comprising:

determining the y-pointing error for each beam arranged in a column along the y-axis;

accomplishing N distinct scans across a row of wells of a microplate with a beam along the x-axis, each scan having a spatial separation from any adjacent scan along the y-axis of $\Delta s$, and each scanned row having the center of the N scans offset from an ideal (i.e., free of pointing error), location, by the y-pointing error ($PE_{actual}$) of the beam for that row; and eliminating scan lines so that the center of the remaining scan lines is $\pm \Delta s/4$, where scan lines are eliminated by calculating the value of equation (1):

$$\text{round}\{PE_{actual}/(\Delta s/2)\} \tag{1}$$

where "round" rounds-off the result in the brackets to the nearest integer, the number of scan lines to be eliminated is proportional to the absolute value of equation (1):

$$|\text{round}\{PE_{actual}/(\Delta s/2)\}|$$

according to:

if round $\{PE_{actual}/(\Delta s/2)\}$ is zero, then no scan lines are eliminated;

if round $\{PE_{actual}/\Delta s/2)\}$ is positive, then the one or more scan lines to be eliminated has the largest y-coordinate (s); or if round $\{PE_{actual}/\Delta s/2)\}$ is negative, then the one or more scan lines to be eliminated has the smallest y coordinate (s).

In embodiments, the column of collimator-microlenses arranged along the y-axis can comprises, for example, from 1 to about 1,000 collimator-microlenses. The scan lines that remain after any scan lines have been eliminated are pointing-error corrected in the y-direction.

In embodiments, N scans can be, for example, from about 1 to about 1,000 scans, from about 2 to about 500 scans, from about 3 to about 300 scans, from about 4 to about 250 scans, from about 5 to about 200 scans, from about 10 to about 100 scans, and like ranges, or any single value therein. In embodiments, N can be, for example, 16 scans for each collimator-microlense. In embodiments, $\Delta s$ can be, for example, from about 5 microns to about 500 microns. The accomplishing N scans and eliminating scan lines can be accomplished, for example, with a programmable computer. The N scans and eliminating scan lines can be accomplished, for example, for a plurality of collimator-microlenses.

In embodiments, eliminating scan lines can comprise, for example, disregarding from 0 to about 5 of 10 scan lines, from 0 to about 5 of 20 scan lines, from 0 to about 10 of 30 scan lines, from 0 to about 10 of 40 scan lines, from 0 to about 10 of 50 scan lines, from 0 to about 10 of 100 scan lines, from 0 to about 20 of 500 scan lines, from 0 to about 100 of 1,000 scan lines, and like ranges and intermediate therein.

In embodiments, the y-axis separation ($\Delta s$) can be, for example, a constant for the N scans. In embodiments, the y-axis separation ($\Delta s$) can be, for example, variable for the N scans and thus one needs to know the variation of $\Delta s$ explicitly. The y-axis separation ($\Delta s$) between respective scan lines can be, for example, from about 5 to about 500 microns.

In embodiments, the y-pointing-error correction can be, for example, improved by from about 50 to about 90 percent compared to an uncorrected collimator-microlense. In embodiments, the y-pointing-error can be reduced by an amount in the range of from about 5 to about 125 microns.

In embodiments, the disclosure provides a system for scanning label independent detection in an optical biosensor, the system comprising:

a microplate having at least one optical biosensor;

a reader-scanner to interrogate the optical biosensor; and a programmable computer to process the interrogation data and to correct beam y-pointing-error in accord with the methods disclosed herein.

In embodiments, the disclosure provides a method for x-axis beam pointing-error correction in an optical reader-scanner having pointing-error, the method comprising:

determining the x-pointing error for each collimator-microlense arranged in a column along the y-axis;

accomplishing N distinct scans across a row of wells of a microplate with a beam along the x-axis, each scan having a spatial separation from any adjacent scan along the y-axis of $\Delta s$, and each scanned row having the center of the N scans offset from an ideal (i.e., free of pointing error), location, by the x-pointing error ($PE_{actual}$) of the beam for that row; and eliminating scan lines so that the center of remaining scan lines is $\pm \Delta s/4$, where scan lines are eliminated by calculating the value of equation (1):

$$\text{round}\{PE_{actual}/\Delta s/2)\} \quad (1)$$

where "round" rounds-off the result in the brackets to the nearest integer, the number of scan lines to be eliminated is proportional to the absolute value of equation (1):

$$|\text{round}\{PE_{actual}/(\Delta s/2)\}|$$

according to:

if round $\{PE_{actual}/(\Delta s/2)\}$ is zero, then no scan lines are eliminated;

if round $\{PE_{actual}/(\Delta s/2)\}$ is positive, then the one or more scan lines to be eliminated has the largest y-coordinate (s); or if round $\{PE_{actual}/(\Delta s/2)\}$ is negative, then the one or more scan lines to be eliminated has the smallest y coordinate (s).

In embodiments, the disclosure provides a system for scanning label independent detection in an optical biosensor, the system comprising:

a microplate having at least one optical biosensor;

a reader-scanner to interrogate the optical biosensor; and a programmable computer to process the interrogation data and to correct beam x-pointing-error in accord with the methods disclosed herein.

In embodiments, the disclosure provides an optical interrogation system comprising:

an illuminator that emits an optical beam towards a biosensor;

a receiver that collects an optical beam from the biosensor and then outputs a signal which corresponds to the collected optical beam; and a processor to process output signals to determine and correct beam x-pointing-error, y-pointing-error, or both x- and y-pointing-error.

In embodiments, the disclosure provides a system for x-, y-, or both x- and y-pointing-error correction in a biosensor image analysis, the system comprising:

a microplate comprising a frame including a plurality of wells formed therein, each well incorporating a biosensor having a surface with a reference region and a sample region;

an optical reader interrogator comprising an optical beam and optics for illuminating a portion of the biosensor, image optics for receiving reflected light from the illuminated biosensor, and an imaging device for capturing a sequence of images from the illuminated biosensor; and a processor to process the sequence of images in accordance with the disclosed methods.

The processors of the disclosed systems can process, for example, 1D, 2D, or both image data acquisition and analysis.

Figure 2:
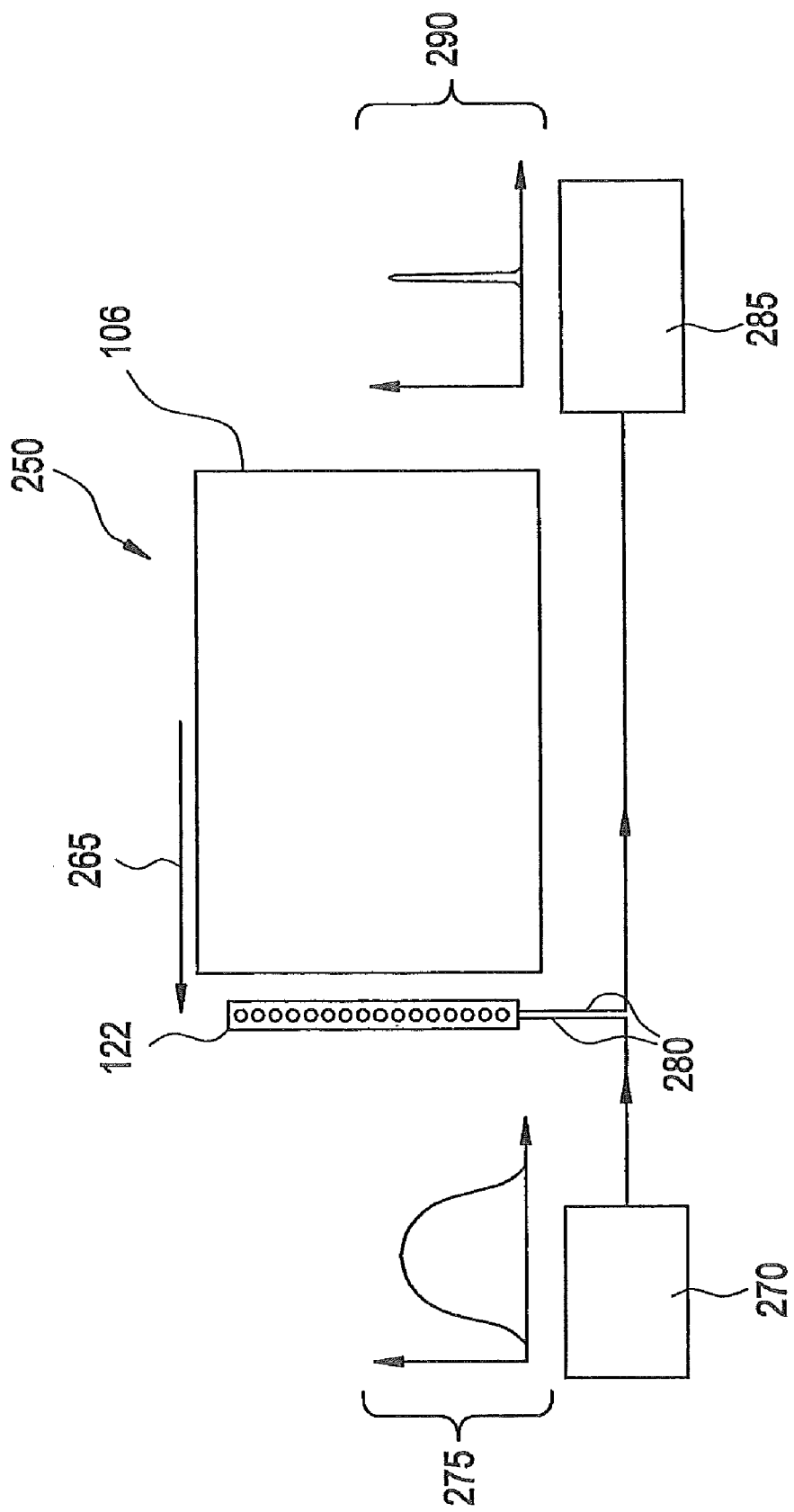
FIG. 2 shows aspects of an imaging system for a scanned optical reader system, in embodiments of the disclosure.

Referring to FIG. 1, there is shown in greater detail a schematic of an exemplary optical interrogation system 100 and associated optical reader system componentry which is capable of interrogating biosensors 102 located within the wells 104 of a microplate 106 that is placed on a holder 108 (XY translation stage 108). The discussion below refers to a 384-well microplate 106, however, any other suitable microplate format can be used. The optical interrogation system 100 includes a light source 110 (e.g., superluminescent diode (SLD)) which can be fiber pigtailed and connected to a variable optical attenuator (VOA) 112 that can be connected to a polarization scrambler 114. The polarization scrambler 114 outputs a light beam which is split by a 1×16 splitter 116 into, for example, 16 individual optical fibers 118. A 1×2 splitter array 120 having, for example, 16 channels connects each optical fiber 118 (e.g., single mode fiber 118) to one of 16 fiber microlenses 122, and as shown in FIG. 2. Each fiber microlense 122 delivers a light beam 124 to a moving biosensor 102 (or static biosensor 102) and also receives a reflected light beam 126. The reflected light beam 126 passes through the 1×2 splitter array 120 and is detected by one of sixteen spectrometers 128. Each spectrometer 128 (optical detection system 128) collects the raw spectral data (interrogation measurements) in the reflected light beam 126 and this raw spectral data is read-out by a personal computer (PC) 130 or like processor device. The PC 130 records the raw spectral data/interrogation measurements as a function of the position of the holder 108 (XY translation stage 108). In addition, the PC 130 analyzes the raw spectral data (interrogation wavelength/angular measurements) which can detect and account for any positional misalignment of a re-positioned microplate 106 and interrogate the biosensors 102. In this interrogation system 100, a wide spectrum light source 110 can be used to illuminate the biosensors 102 and the PC 130 can be used to analyze the resonance spectral content of the normal retro-reflected light beams 126. Alternatively or additionally, if desired an angular optical interrogation system could be used to implement the disclosed method. As shown further in-part in FIGS. 2 and 3, the microplate 106 can be moved across a fixed optical head which holds 16 fiber microlenses 122 and each fiber microlense 122 emits one optical beam 124 which interrogates the biosensors 102 in one row on the microplate 106. A precision X/Y translation stage 108 can be used to move the microplate 106. A typical 384-well format microplate 106 can be, for example, approximately 3 inches in width and 5 inches in length. Hence, to read the entire microplate 106, the X/Y translation stage 108 may move up to 125 mm in distance along the x dimension of the microplate 106, but typically less than 4.5 mm in the y-dimension since 16 lenses 122 are linearly arranged along the y-dimension. In this example, the X/Y translation stage 108 contains an optical encoder that provides pulses for every 200 nm of motion. The PC 130 tracks and records these pulses so that the absolute position of the X/Y translation stage 108 holding the microplate 106 is known at any given time during the interrogation of the biosensors 102 within the microplate 106.

Referring to FIG. 2 there is shown an exemplary scanned reader 250 having a lense array 122 with, for example, a series of 16 optical beams, one for each biosensor row (not shown) on the microplate 106. The microplate 106 can be scanned across lense array 122 in the direction 265. A light source 270 having, for example, a broadband spectrum 275 (power v. $\lambda$ curve) illuminates the lense array and the microplate 106. The lense array delivers light via optical fibers 280. The lense array also receives or acquires reflected resonance light and transmits this as power and wavelength information (power v. λ curve) 290 as a function of position within each well via optical fibers 280 to spectrometer(s) 285. A processor processes the information 290 to output a binding signal (wavelength change) as a function of time. In the configuration shown the light beams can strike the plate from below at normal incidence, and the spot size is nominally 100 micrometers ($1/e^2$ diameter). Other suitable incidence angles and spot sizes can be used.

Figure 3:
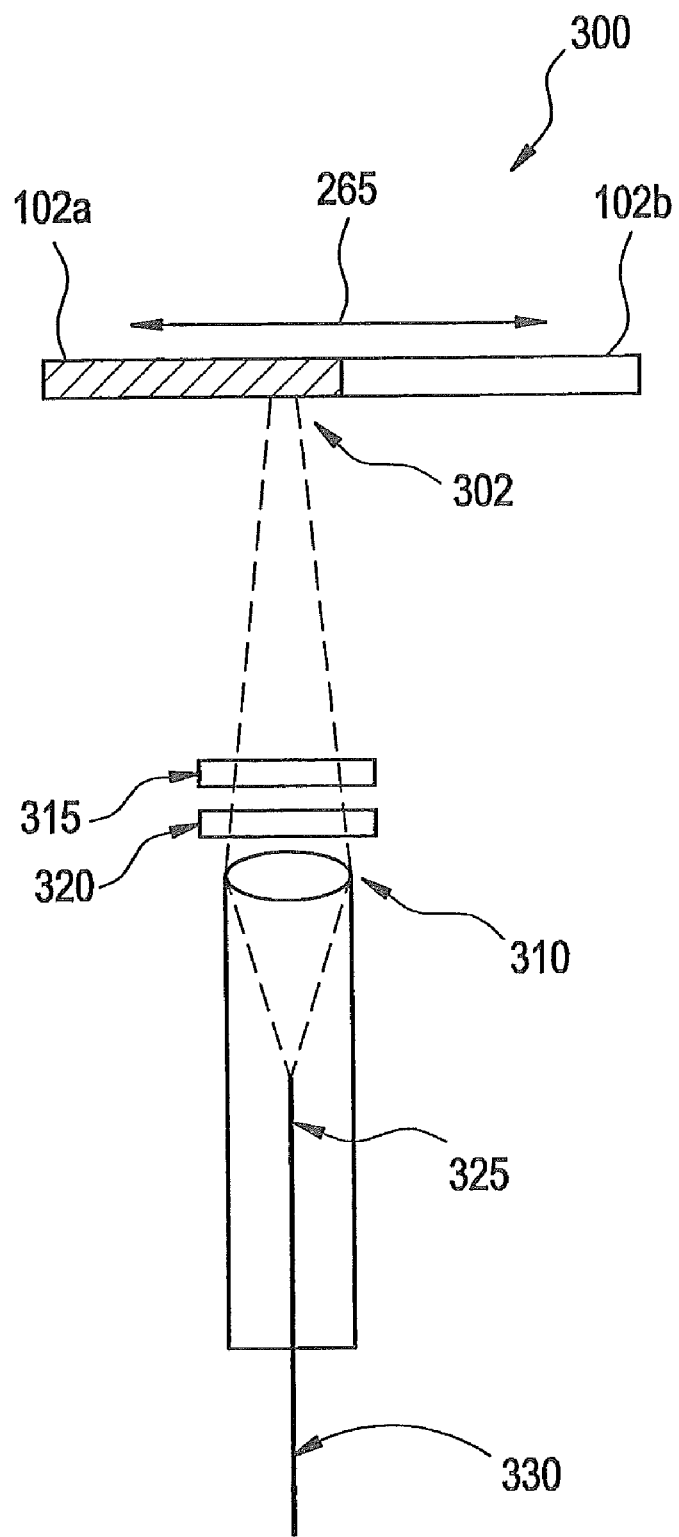
FIG. 3 shows additional aspects of a normal incidence optical imaging configuration of a scanned label independent optical reader system, in embodiments of the disclosure.

Referring to FIG. 3 there is shown a portion of a scanned reader where a microplate 106 having a biosensor 102 which further has a binding region 102a and a reference region 102b can be interrogated by uni- or bi-directional scanning 265 with, for example, a normal incident optical system 300 which provides, for example a 100 micron diameter scanning spot 302 on the biosensor's 102 back-side surface. The normal incident optical system 300 includes a lens 310, a quarter wave plate (λ/4) 315, a linear polarizer 320, a single mode (SM) fiber 325 which connects up to-and-from a 1×2 fiber splitter 330.

The optical path components for an individual beam are shown in FIG. 3. In embodiments, an optical isolator can be used to suppress Fresnel back reflections from the microplate. This isolator can be created above the lens by placing a linear polarizer and then a λ/4 plate. Additional details of isolator optics is disclosed in, for example, U.S. Pat. No. 7,239,395, assigned to Corning Inc.

The lenses that can be used are, for example, GRIN lenses 310 having a focal length of 1.81 mm. The working distance of the lens can be, for example, about 33 mm, and the spot size created can be, for example, 100 microns ($1/e^2$) diameter.

Since "pointing error" is encountered due variations in the lens package the exact location of the illumination spots on the microplate is not separated by exactly the 4.5 mm grating spacing. The optical axis of the lens and the mechanical axis of the package that holds the lens are rarely if ever perfectly aligned. Thus when a lens is aligned for maximum received power, i.e., normal incidence, the spot that strikes the microplate will be off from the desired or nominal beam location by about ($\Delta\theta*z$), where $\Delta\theta$ is the pointing-error angle and z is the lens-to-plate spacing (e.g., about 33 mm). Typical pointing-error at the microplate is about 100 microns.

Figure 4:
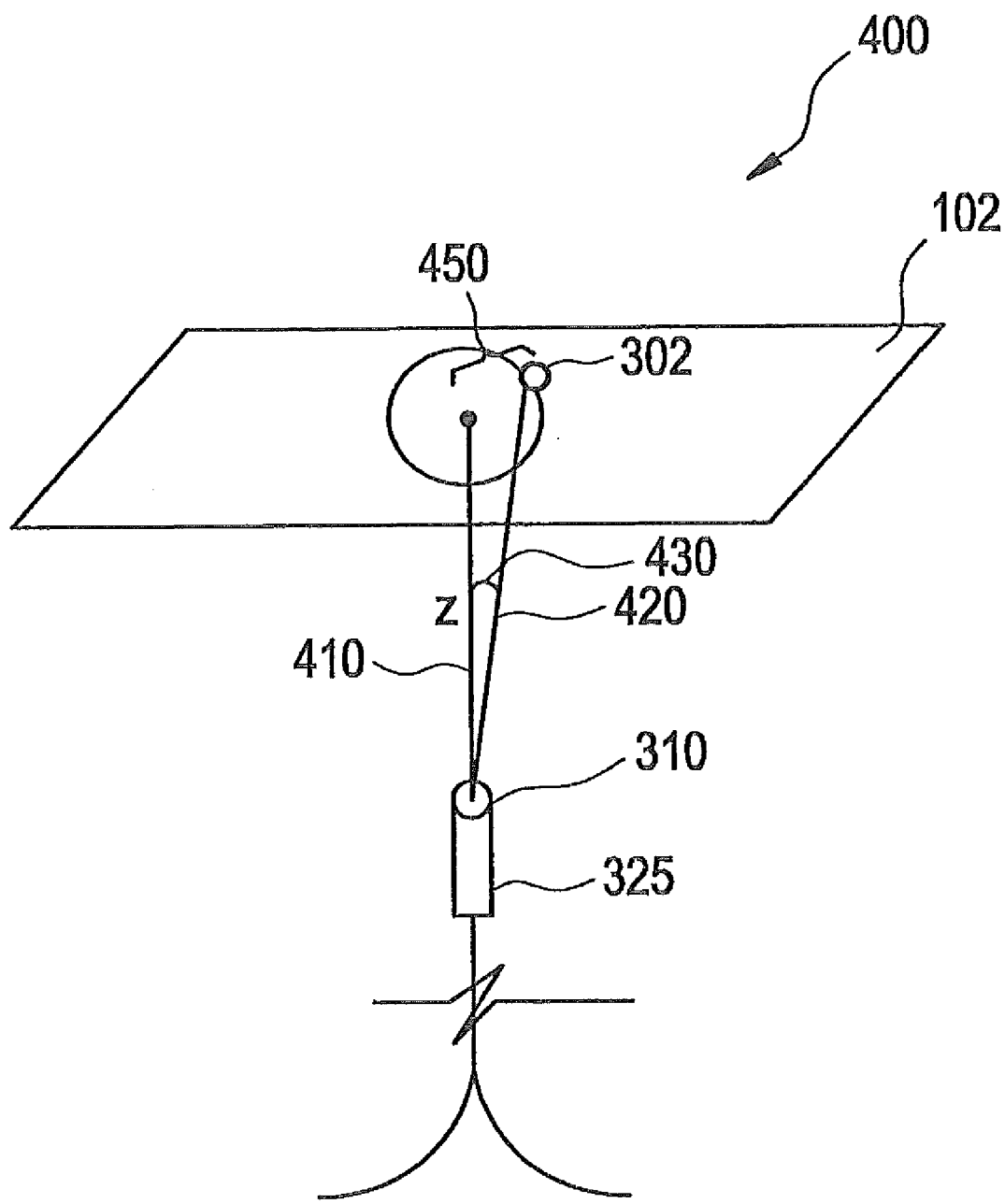
FIG. 4 shows a basis for pointing-error arising from variation in scan-beam spot location on a biosensor, in embodiments of the disclosure.

Referring to FIG. 4 there is illustrated a basis for scanner spot pointing-error which arises from variation in the scan beam spot location as found in, for example, a normal incidence optical imaging configuration of a scanned label independent detection optical reader system 400. The normal incidence optical system including lens 310 and a single mode fiber 325 provides, for example an actual scanning spot 302 on the biosensor's 102 back-side surface or the grating. The actual beam spot 302 resulting from actual beam 420 is typically randomly displaced or offset from an ideal spot location 410 by an amount $\Delta\theta$ 430. The difference amount $\Delta\theta$ 430 is manifested on the flat biosensor surface 102 as the displacement difference or separation, or pointing-error. The pointing-error 450 is believed to be caused by misalignment of the system's optical and mechanical components. An impact of the lens pointing-error is that as a plate is scanned, the grating biosensors "appear" to be offset in either the x- or y-dimension. Since each microplate row is measured by a common lens, any given row of the microplate will have gratings that appear offset by a consistent amount from any other row.

Figure 5:
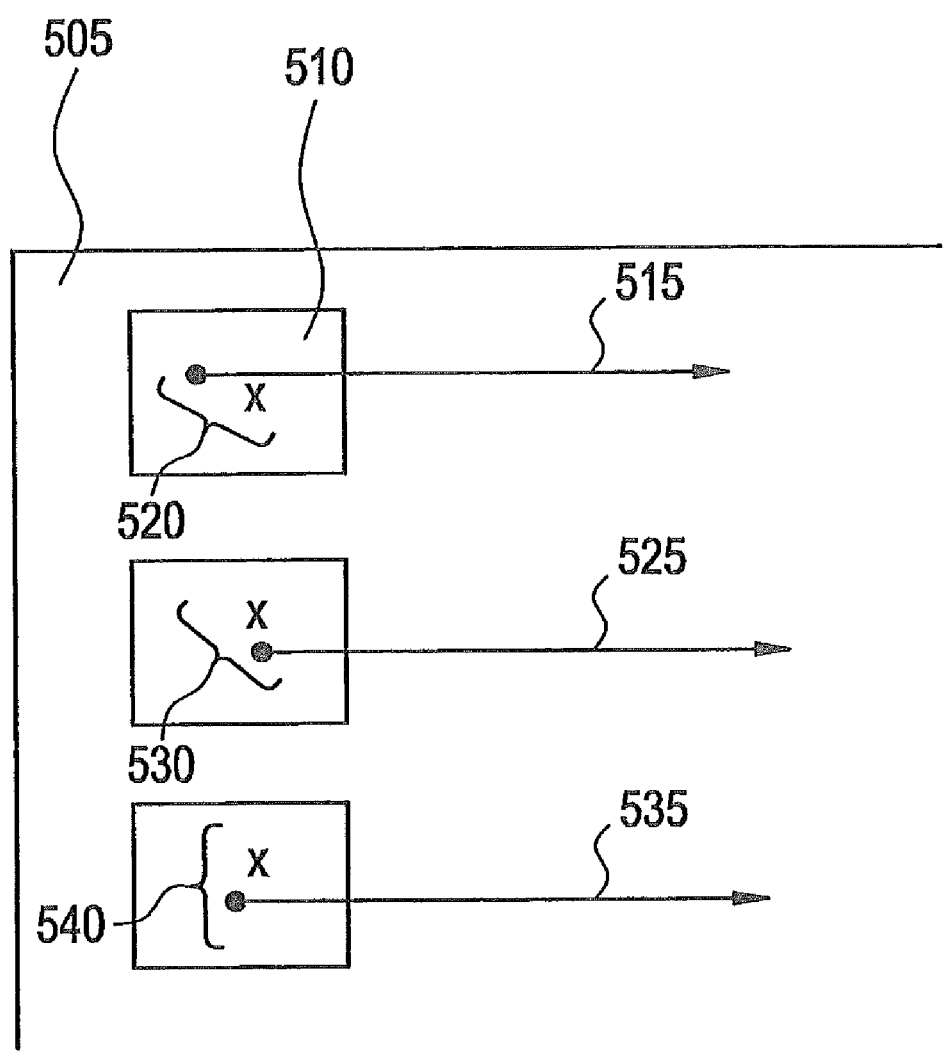
FIG. 5 shows further aspects of pointing-error arising from beam location error on a biosensor, in embodiments of the disclosure.

Referring to FIG. 5 there is illustrated further aspects of pointing-error arising from beam location error in both the x- and y-directions at the biosensor's gratings. Thus, a biosensor 505 having grating 510 is interrogated with a first (A) illuminating scan beam 515 which results in pointing-error 520 (or 450 as described in FIG. 4). Similarly, biosensor 505 having grating 510 is interrogated with a second (B) illuminating scan beam 525 which results in pointing-error 530, and biosensor 505 having grating 510 is interrogated with a third (C) illuminating scan beam 535 which results in pointing error 540; and so on for like beam scans.

Figure 6:
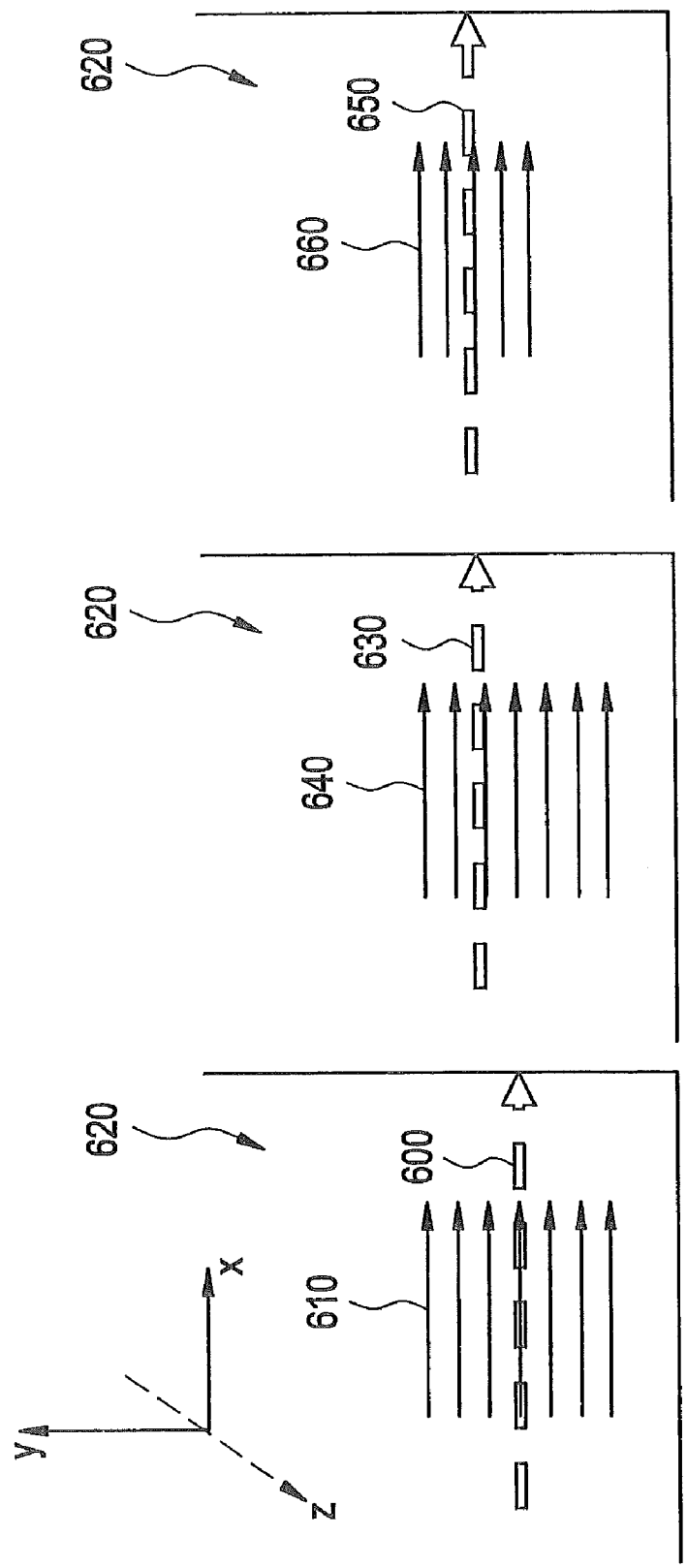
FIGS. 6A to 6C illustrate scan locations schemes across a biosensor and the associated beam collimator pointing-error, in embodiments of the disclosure.

6A to 6C illustrate scan locations across a sensor region and associated beam pointing-error. In FIG. 6A the dashed arrow 600 shows an idealized location for the center of a 2D series of scans across a sensor region 620. Arrows 610 indicate the location of seven scan lines (e.g., about 100 microns apart) when the collimator pointing error is 0 microns. In FIG. 6B the dashed arrow 630 also shows a similar idealized center of a 2D series of scans. The arrows 640 then indicate the location of the seven scan lines (about 100 microns apart) when the collimator pointing error is about −120 microns. FIG. 6C has a dashed arrow 650 again showing an idealized center of a 2D series of scans across a sensor region 620 for the series of 2D scans 660, and is the same as in FIG. 6B with the exception that, for example, the lowest two scan lines have been excluded, i.e., as part of the pointing-error correction calculation. Here there are only 5 scan lines 660. However, the center of these scan lines is only about 20 microns away from the ideal location 650 yielding an effective change in y-axis pointing-error of, for example, from about −120 microns to about −20 microns or about 83% (120−20/120=0.83). In embodiments, an effective change or correction in y-axis pointing-error can be, for example, from about −100 microns to about −25 microns or about 75%.

Figure 7:
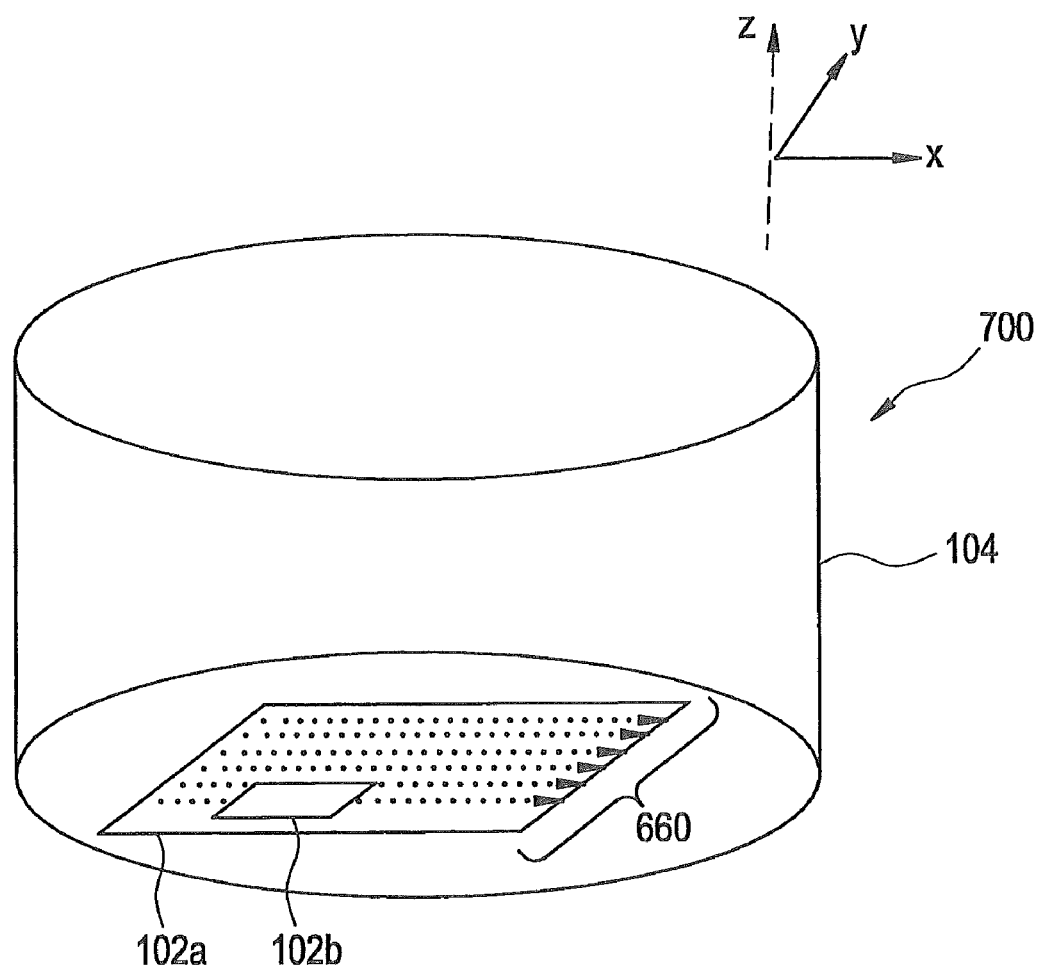
FIG. 7 shows a perspective view of a microplate well having a biosensor and representative beam scan lines, in embodiments of the disclosure.

FIG. 7 in perspective shows a portion of a microplate 700, specifically a well 104 having a biosensor sample region 102a, an optional reference region 102b, and a representation of a series (arrows) of optical beam scans 660 that can be accomplished across the biosensor's surface on a side opposite of the sample and reference surface side. Pointing-errors can complicate any data analysis since the pointing-error of the lens must be taken into account if one desires to integrate a specific spatial region of each well. The effect of lens pointing-error along the scan axis (x-axis) is illustrated in FIG. 8A.

Figure 8A:
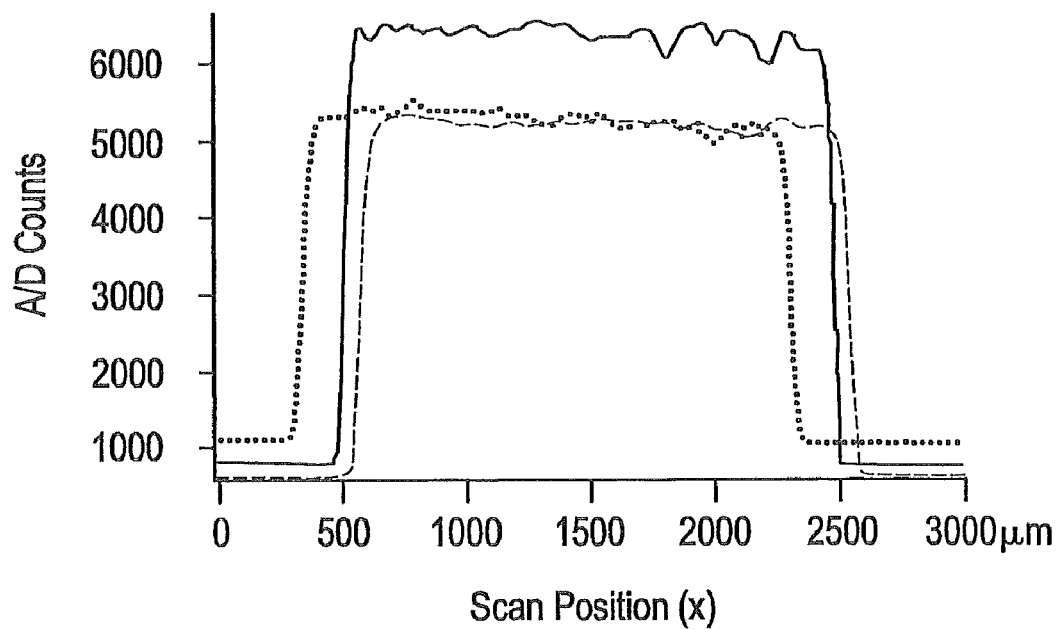
FIGS. 8A and 8B respectively show representative power versus position traces for uncorrected or comparative scans, and pointing-error corrected scans, in embodiments of the disclosure.
Figure 8B:
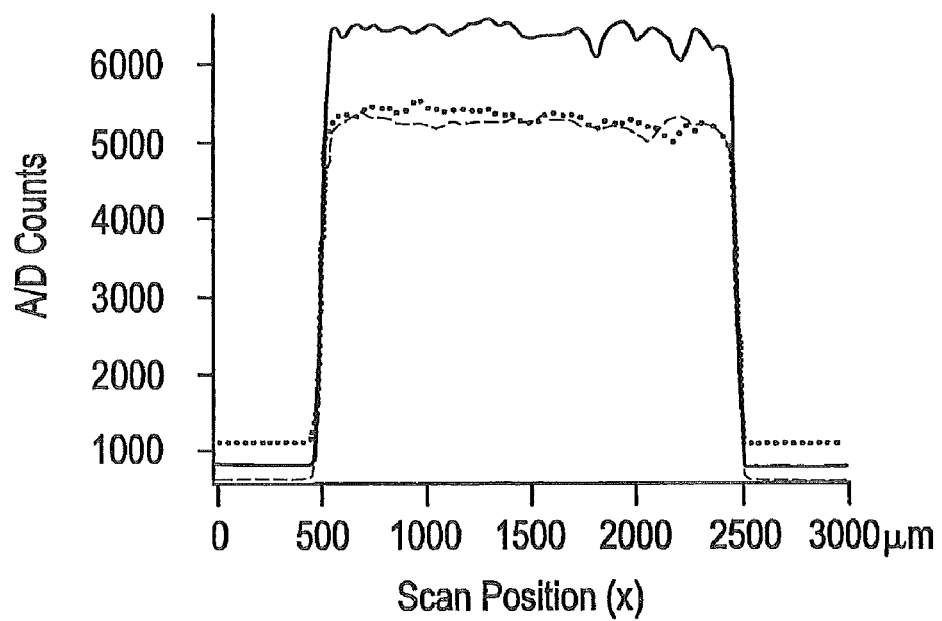

FIG. 8A shows an exemplary composite presentation of power versus position traces for uncorrected or comparative scans of three separate wells. Power is in A/D counts ($10^3$) and scan position is in microns. FIG. 8B shows the power versus position traces for exemplary x-pointing-error corrected scans of three separate wells. Comparing the power versus position traces of FIG. 8A and FIG. 8B demonstrates improved pointing-error, that is a reduction in pointing-error, as a result of aligning the edges of the biosensor grating using the method of the disclosure to remove the deleterious effects of lens pointing-error along the scan direction. Similarly, exemplary y-pointing-error corrected scans of the reference regions, and the sample or signal regions can be generated (data not shown).

In embodiments, a solution to the problem of pointing error involves two aspects. First, the lenses are "clocked", or rotated, so that the majority of their respective pointing-error appears preferentially along the scan axis (x-axis) of the microplate. Second, the x-pointing-error of each lens is measured by observing when the edge of a grating "appears" or is reached as the plate is scanned. Along a given column, all of the gratings should appear at the same time if there was no pointing-error. The pointing-error of each lens is recorded into a database on the machine. Since the plate is scanned along the x-direction, the recorded data may be offset by the known pointing-error, see for example, FIG. 8B. Hence the pointing-error may be reduced to a level of about 1 pixel or about 12 microns, for example, in an Epic® reader system. This can be automatically accomplished by a scanned label-independent reader before the analysis of signal and reference regions is performed. Pointing-error may also be reduced in the y-direction if 2D data can be or has been acquired.

Figure 9:
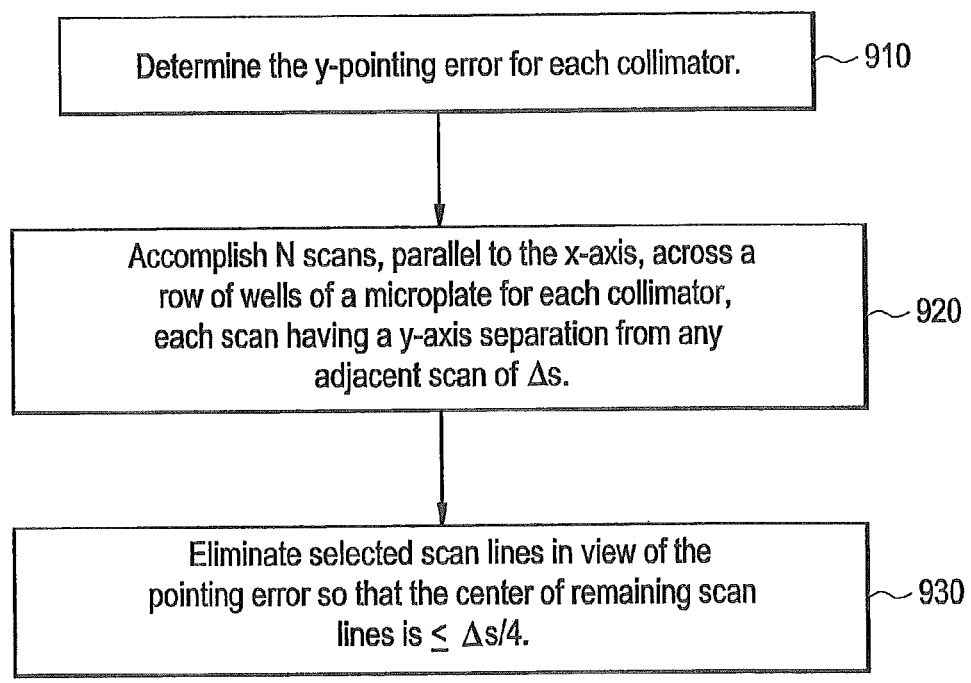
FIG. 9 shows a flow chart summary of the y-pointing-error correction method in an optical reader-scanner system, in embodiments of the disclosure.

FIG. 9 shows a flow chart summary of the disclosed method for pointing-error correction in an optical reader-scanner system. First, one determines the y-pointing error for each collimator, 910. Next, simultaneously accomplish N scans, parallel to the x-axis, across a row of wells of a microplate for each collimator, each scan having a y-axis separation from any adjacent scan of $\Delta s$, 920. Finally, eliminate selected scan lines in view of the pointing-error correction criteria, as disclosed and illustrated herein, so that the center of remaining scan lines is $\leq \Delta s/4$, 930. The above-mentioned subroutine for eliminating selected scan lines in view of the pointing-error includes calculating the value given by equation (1):

$$\text{round}\{PE_{actual}/(\Delta s/2)\} \quad (1)$$

where "round" refers to rounding-off the result obtained within the brackets $\{PE_{actual}/(\Delta s/2)\}$ to the nearest integer.

If the result of "round $\{PE_{actual}/(\Delta s/2)\}$" is zero, then no scan lines are eliminated.

If the result of "round $\{PE_{actual}/(\Delta s/2)\}$" is positive, then the scan line or line(s) eliminated include those having the largest y-coordinate(s).

If the result of "round $\{PE_{actual}/(\Delta s/2)\}$" is negative, then the scan line or line(s) eliminated include those having the smallest y-coordinate(s).

The number of scan lines that can be eliminated is given by the absolute value of the result of the "round $\{PE_{actual}/\Delta s/2\}$" calculation above. After the scan lines, if any, have been removed in accordance with the above criteria, the remaining scan lines will be "y-pointing-error corrected", that is they will have reduced pointing-error in the y-direction.

The disclosed system and method for biosensor substrate image analysis are useful for performing, for example, diagnostic or therapeutic assays such as scanning label-independent detection. In embodiments, one or more biosensors can be situated in a well of a microplate and the disclosed system and method can be used to interrogate one or more of the biosensors to provide binding information between the biosensor surface, such as an immobilized cell or receptor mimic, and a binding target or partner.

In embodiments of the disclosure, a Corning Epic® label-independent detection system can be used as a label-independent biochemical binding detection system. It can consist of a 384-well microplate with optical biosensors within each well, and an optical reader to interrogate these microplates. Each well can contain a small, e.g., about 2 mm×2 mm, optical grating, known as a resonant waveguide grating (RWG). The wavelength of the light reflected by the grating is a sensitive function of the optical refractive index at the surface of the sensor inside the well. Hence when material such as a protein, antibody, drug, cell, or like material binds to the well bottom surface or sensor surface, the reflected wavelength will change.

The optical reader uses a series of focused optical beams that are scanned across the bottom of the microplate to measure reflected wavelength from each optical sensor. The reader may be used to monitor changes in the reflected wavelength from each sensor as a function of time. It may also be used to evaluate wavelength or changes in wavelength as a function of position within each sensor, that is, spatially resolved or imaging information.

When biochemical material binds to the surface of a sensor, this alters the local refractive index, and the wavelength reflected by the optical sensor changes. The reader detects and quantifies this wavelength change in order to measure biochemical events within each well. Light that impinges upon the sensor is resonantly coupled into the waveguide only if it has the appropriate combination of wavelength and incident angle (i.e., wave vector.)

By monitoring the reflected wavelength (or angle) as a function of time, one may determine if material has bound to or been removed from the surface of the sensor. A typical assay is performed by first immobilizing a protein to the surface of microplate. Then a baseline read is performed where the wavelength reflected by each of the sensors in the plate is measured and recorded. Then a binding compound (i.e. drug) is added to the wells, and a second wavelength read is made. The wavelength shift that occurs between the two reads is then a measure of how much drug bound to each sensor of the microplate.

In embodiments, a portion of each sensor can be chemically or physically blocked to, for example, prevent binding, to act as a reference signal for removing false wavelength shifts that arise from environmental changes such as bulk refractive index changes, material drift, non-specific compound binding, or thermal events. The interrogation system must be able to distinguish the signals from the binding/reference regions, each of which may occur at almost any wavelength within the sensor bandwidth, and are of the same polarization. In embodiments, intra-well references, where a small portion of each well can be chemically blocked to act as a spatially local reference.

Thus, in embodiments, a broadband superluminescent diode (SLD) light source can be coupled into a single mode optical fiber. The light is then sent through a polarization scrambling element, and a variable optical attenuator (VOA) to allow for power control. Light can then be split into 16 fibers that ultimately feed light into the 16 optical lenses. A 1×2 fiber optical splitter can be positioned just before each lens, to allow retro-reflected light to be redirected to a series of spectrometers. Each spectrometer monitors the light reflected back from one lens, which in turn interrogates one row of the microplate as the plate is scanned across the optics. Isolator optics can optionally be placed on top of the lenses to suppress Fresnel (non-resonant) reflections. As a given optical beam traverses a grating, an optical spectrum is captured. This spectrum contains an optical resonance. The centroid (nominal wavelength) of this resonance is measured, along with the peak amplitude.

The wavelength and peak power are then recorded as a function of time as the beams are scanned across each grating. If one knows the spatial pattern of the scan, this time information can be converted into (x,y) position (a spatial pixel).

In embodiments, the optical beams may be scanned in any other suitable manner. For example, the scans may take a 1D slice across a grating, they can be raster scanned to produce a 2D image, or like patterns, and combinations thereof. The format of the spatial scan can be readily changed by the user if desired via the reader software.

The aforementioned imaging reader system can have a spatial resolution determined by the optical beam size (e.g., 100 microns $1/e^2$ or 58 microns FWHM). Regions of arbitrary size and shape may be averaged together. This may be done after data has been acquired such as in a post-processing technique. Thus, the sensors can be re-analyzed in multiple ways once data is acquired.

The Corning Epic® label-independent detection system can include an optical reader that interrogates, for example, microplates containing resonant waveguide grating biosensors, and evaluates biochemical binding on the sensors by detecting spectral shifts in reflected wavelength. The magnitude of these wavelength shifts ranges, for example, from about 2,000 picometers (pm) for large protein/antibody interaction or attachment to about 1 pm for small drug binding. A scanned label-independent detection reader translates small (such as less than 100 microns) diameter optical beams across the microplate, and obtains spatially resolved wavelength data in either one or two dimensions from each well. In embodiments, a super-luminescent diode light source can be used to illuminate the sensors and spectrometers to measure the reflected resonance wavelength. As an imaging reader, it can use plates with chemically blocked (reference) sub-regions, or with patterns of protein within the well's (signal) sub-regions. In embodiments, the reader can also actively control the microplate position to, for example, less than about 200 nanometers to minimize wavelength shifts induced by plate removal events, see for example the aforementioned U.S. patent application Ser. Nos. 11/210,920, and 60/844, 736. The disclosed system can accomplish high-throughput screening methods, such as for drug compounds, including having excellent sensitivity (e.g., detecting about 1 pm level binding events), read speed (e.g., about 1 minute per plate read), and plate in/out capability. This system can incorporate various design considerations or options, optical system components, noise performance, and operational modes.

In embodiments, the method of the disclosure can be further illustrated and described below including the working examples.

Although this disclosure may be useful for detection using labeled ligands it is particularly well suited for biosensors based on label-free or label-independent detection (LID) methods such as a resonant waveguide (RWG) optical biosensor, for example, Corning Incorporated's Epic® system or those based on surface plasmon resonance (SPR).

In embodiments, the sensor can be, alternatively or additionally, spectrally interrogated, that is where the sensor is interrogated at a fixed incidence angle with a broad spectral source and that the wavelength is detected in the reflected beam. The source is then a broad spectral source and the detector is a wavelength sensitive detector such as a spectrometer. In embodiments, however, the sensor can be angularly interrogated where the sensor is interrogated with monochromatic light and then a resonant angle is detected in the reflected beam.

EXAMPLES

The following examples serve to more fully describe the manner of using the above-described disclosure, and to further set forth the best modes contemplated for carrying out various aspects of the disclosure. It is understood that these examples do not limit the true scope of this disclosure, but rather are presented for illustrative purposes.

The disclosed system and method for providing an image analysis correction to the y-axis pointing-error can be illustrated by a graphic example. In this example, the 2D scans that interrogate the reference region of a microplate well can be equally spaced apart, such as about 100 microns in y, and consist of seven individual scans as illustrated in FIGS. 6A and 6B.

Example 1

POINTING-ERROR MEASURED WITH A CCD DETECTOR With a commercially available CCD detector, the following steps were accomplished to determine the collimator's pointing error:

a) A series of beam collimators (e.g., 16) was arranged so that each beam collimator was equally spaced in a column (y-direction) with a spacing of, for example, about 4.5 mm.

b) A CCD chip was positioned at the intended use distance, for example, about 31 to about 35 millimeters away from the first collimator. The size of the CCD coverage area was larger than the expected location of the entire spot based on the maximum expected pointing error. In embodiments, the size of the CCD coverage area can be, for example, about 12 by about 15 millimeters, the spot size can be, for example, about 100 microns×(1/e$^2$), the "expected location" for the spot can be, for example, about ±300 microns in x- or y-, and the "maximum expected pointing error" can be, for example, about +300 microns in x- or y-. The rows and columns of the CCD array should be aligned parallel to the respective x- and y-directions.

c) Light was transmitted by the first collimator and the spot intensity was measured with the CCD detector. The location of the spot was calculated by determining the centroid (e.g., "center of mass" calculation). The x any y positional coordinates (e.g., in microns) of the centroid were recorded. The center of the CCD array was assigned x- any y-positional coordinates (0,0).

d) The CCD detector was translated 4.5 mm along the y-axis in the direction of the next collimator.

e) Steps c) and d) were repeated for each of the remaining 15 collimators.

f) The x-positions for the two collimators with the largest and smallest x-values were averaged.

g) The difference between this average position and the position for collimator 1 was determined and was defined as the x pointing-error for collimator 1.

h) Step g) was repeated for each of the remaining 15 collimators.

i) The y-positions for the two collimators with the largest and smallest y-values were averaged.

j) The difference between this average position and the position for collimator 1 was determined and was defined as the y pointing-error for collimator 1.

k) Step j) was repeated for each of the remaining 15 collimators.

Example 2

POINTING-ERROR MEASURED WITH A MICROPLATE In an exemplary microplate, for example, a 384-well microplate having square 2 mm×2 mm biosensors arranged in a 16×24 array, the following were accomplished to determine the y-axis collimator pointing error. The spacing between the gratings is equal to about 4.5 millimeters in x- and y-.

a. A series of beam collimators (e.g., 16) were arranged in a y-direction column or linear array that had equal separation between beam collimators of, for example, 4.5 mm.

b. A microplate was positioned at the use distance away from this collimator array such that one column of 16 biosensors on the microplate was nominally centered over the column of 16 collimators.

c. Light was transmitted by the 16 collimators, reflected off the 16 biosensors, recollected by the 16 collimators, and then sent to 16 spectrometers.

d. The microplate was then translated in the positive (+) y-direction such that the light from each collimator no longer strikes any sensor (e.g., 3 mm).

e. The microplate was then scanned in the negative (−) y-direction so that the light from each collimator first strikes a lead edge of the sensor, then the middle of the sensor, and then the opposite or trailing edge of the sensor, and scanning was continued until the light from each sensor no longer struck the sensor. The reflected power as a function of scan position was recorded for each collimator.

f. For each collimator the location of the initial or first edge of the sensor was determined by finding a point where the intensity rose to one-half of the value it had when the beam was fully on the sensor.

g. For each collimator the location of the second edge of the sensor was determined by finding a point where the intensity declined to one half of the value it is when the beam was fully on the sensor.

h. For each collimator the average location of the first and second edges was found. The average was the location for each collimator.

i. The average location of all 16 collimators was found.

j. The y pointing-error for collimator 1 was the difference between the collimator location and the average location of the two collimators with the largest and smallest location.

k. Step j) was repeated for the remaining 15 collimators.

Example 3

X-Pointing-Error The x-pointing-error can be determined using the steps a. through k. in Example 2 with the exception of substituting "x" for "y".

Example 4

Y-Pointing-Error Correction The value of the y-pointing error for each beam collimator is first measured and determined according to, for example, either Example 1 or 2 above. Next the Y-Pointing-Error Correction is accomplished according to the following steps.

1) 16 beam collimators were arranged in a line or column and are numbered sequentially 1 to 16. The arranged beam collimators were along the y-axis. The y-coordinate of beam collimator 1 had the largest y-coordinate value of all the beam collimators. Beam collimator 2 had the next largest y coordinate value and continuing until beam collimator 16 had the lowest y-coordinate value.

2) N distinct scans of the microplate were made with a separation in y-coordinate of Δs. The motion of the microplate has created N scans across the wells in row A with collimator 1; N scans across the wells in row B with collimator 2, . . . , and N scans across the wells in row P with collimator 16. Therefore, each collimator is associated with N scans.

3) For each scanned row, the center of these scans (in the y-direction) is offset or "in-error" from the ideal location by the pointing error, $PE_{actual}$, of the collimator for that row.

4) By eliminating scan lines the effective pointing-error is reduced. Alternatively or additionally, by eliminating scan lines the effective pointing-error is corrected. Each time a scan line is eliminated, the center of the remaining scan lines changes by Δs/2. Scan lines are selectively removed in accordance with the disclosure so that the center of the remaining scan lines is ±Δs/4.

To eliminate scan lines calculate the value given by equation (1):

$$\text{round}\{PE_{actual}/(\Delta s/2)\} \tag{1}$$

where "round" refers to round-off of the result in the brackets to the nearest integer. The number of scan lines that can be eliminated is given by the absolute value of the result of the "round$\{PE_{actual}/(\Delta s/2)\}$" calculation above.

If the result of "round$\{PE_{actual}/(\Delta s/2)\}$" is zero, then no scan lines are eliminated.

If the result of "round$\{PE_{actual}/(\Delta s/2)\}$" is positive, then the eliminated scan line(s) is (are) the one (or ones) with the largest y-coordinate(s).

If the result of "round$\{PE_{actual}/(\Delta s/2)\}$" is negative, then the eliminated scan line(s) is (are) the one (ones) with the smallest y-coordinate(s).

5) After the scan lines, if any, have been removed in accordance with the above criteria, the remaining scan region will be "pointing-error corrected", that is its average y-coordinate will have a reduced deviation from the intended location. In a specific example, scan lines can also be evaluated and eliminated according to the following conditional criteria:

a. If $|PE_{actual}| \leq \Delta s/4$ then no scan lines are removed.

b. If $PE_{actual}$ is positive and greater than +Δs/4, then:
  i. If $+\Delta s/4 < PE_{actual} \leq +3\Delta s/4$, then the most positive y-scan line is eliminated;
  ii. If $+3\Delta s/4 < PE_{actual} \leq +5\Delta S/4$, then the 2 most positive y-scan lines are eliminated; or
  iii. If $+5\Delta s/4 < PE_{actual} \leq +7\Delta S/4$, then the 3 most positive y-scan lines are eliminated.

c. If $PE_{actual}$ is negative and less than −Δs/4 then:
  i. If $-3\Delta s/4 < PE_{actual} \leq -\Delta s/4$, then the most negative y-scan line is eliminated;
  ii. If $-5\Delta s/4 < PE_{actual} \leq -3\Delta s/4$, then the 2 most negative y-scan lines are eliminated; or
  iii. If $-7\Delta s/4 < PE_{actual} \leq -5\Delta s/4$, then the 3 most negative y-scan lines are eliminated.

Example 5

X-Pointing-Error Correction The x-pointing-error correction can be determined using the steps a. through k. in Example 4 with the exception of substituting "x" for Example 6

X- AND Y-Pointing-Error Correction Examples 1 and 2 above were repeated with the exception that they were accomplished simultaneously or sequentially.

Comparative Example

When scans of a well in a microplate were made (as is shown in FIG. 8A), each data point collected, whether a power data point (as shown in FIG. 8A) or a wavelength (not shown), was assigned a position within the well (as indicated on the horizontal axis in FIG. 8A). For example, in FIG. 8A, a position of 1,500 microns (μm) corresponds to the midpoint of the scan of the reference region. If the pointing-error is zero, then the datum obtained at the 1,500 μm position point is obtained from the center of the well. If the pointing-error is not zero (and the pointing error is not corrected) the datum collected at the 1,500 μm position is obtained at a position different from the center of the well. This different position is equal to 1,500 μm plus the pointing error of the collimator that is used in the measurement. Therefore, if the pointing-error correction is not performed, the position assigned to each datum is in error by an amount equal to the pointing-error. FIG. 8B shows the same scans as in FIG. 8A except that the pointing error has been corrected to within one pixel (about 12 μm in this example). Thus, the error in position using the corrected scans in FIG. 8B is much less than that in FIG. 8A.

If the pointing-error correction is not performed (in either the x- or y-direction) then the accuracy with which an interrogation datum can be assigned to a given location (in the x- or y-direction) within a well is reduced. The result of this type of error in location can result in sampling a region that is not intended. For example, a reference region has a specific size and the interrogated region may be displaced relative to this location resulting in some or all of the sampled points residing outside the desired region. The data points collected outside the intended region could result in an error in the quantity being measured by the interrogation.

Alternatively, without pointing-error correction, an interrogated region might need to be smaller than desirable in order to ensure that all collected points reside within that region. This, however, reduces the potential number of points that could have been sampled, thereby reducing the accuracy of the measurement.

The disclosure has been described with reference to various specific embodiments and techniques. However, it should be understood that many variations and modifications are possible while remaining within the spirit and scope of the disclosure.

What is claimed is:

1. An optical interrogation system having scan beam pointing-error correction, comprising:
   an illuminator that emits an optical scan beam at normal incidence towards a biosensor;
   a receiver that collects the optical beams at normal incidence from the biosensor and then outputs a signal which corresponds to the collected optical beam; and
   a processor to process the output signals from the receiver to determine and correct the optical beam x-pointing-error, y-pointing-error, or both x- and y-pointing-error, wherein beam pointing error is corrected by numerically eliminating selected optical beam scan lines received from the biosensor, and the optical beam scan lines are numerically selected for eliminating by disregarding a beam scan line if the scan line does not include a selected region of the biosensor.

2. The system according to claim 1 wherein the processor processes 1D-, 2D-, or both 1D- and 2D-image data acquisition and analysis.

\* \* \* \* \*